US008426586B2

(12) United States Patent
Soyka et al.

(10) Patent No.: US 8,426,586 B2
(45) Date of Patent: Apr. 23, 2013

(54) PROCESS FOR PREPARING AMINO CROTONYL COMPOUNDS (75) Inventors: Rainer Soyka, Biberach (DE); Werner Rall, Mittelbiberach (DE); Juergen Schnaubelt, Oberhoefen/Warthausen (DE); Peter Sieger, Mittelbiberach (DE); Christian Kulinna, Attenweiler (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1851 days.

(21) Appl. No.: 11/457,622

(22) Filed: Jul. 14, 2006

(65) Prior Publication Data

US 2007/0027170 A1 Feb. 1, 2007

Related U.S. Application Data (63) Continuation of application No. 10/941,116, filed on Sep. 15, 2004, now abandoned.

(60) Provisional application No. 60/517,777, filed on Nov. 6, 2003.

(30) Foreign Application Priority Data

Oct. 17, 2003 (DE) .................................. 103 49 113

(51) Int. Cl.
*C07D 239/84* (2006.01)
*C07D 215/44* (2006.01)

(52) U.S. Cl.
USPC .......................................... 544/153; 546/153

(58) Field of Classification Search .................. 544/153; 546/153
See application file for complete search history.

(56) References Cited

U.S. PATENT DOCUMENTS

| 6,127,374 | A | 10/2000 | Bridges |
| 6,297,258 | B1 | 10/2001 | Wissner et al. |
| 6,627,634 | B2 | 9/2003 | Himmelsbach et al. |
| 6,972,288 | B1 | 12/2005 | Himmelsbach et al. |
| 7,019,012 | B2 * | 3/2006 | Himmelsbach et al. . 514/266.22 |
| 7,220,750 | B2 | 5/2007 | Himmelsbach et al. |
| 7,846,936 | B2 | 12/2010 | Hilberg et al. |
| 7,960,546 | B2 | 6/2011 | Schroeder et al. |
| RE43,431 | E | 5/2012 | Himmelsbach et al. |
| 8,188,274 | B2 | 5/2012 | Schroeder et al. |
| 2002/0169180 | A1 | 11/2002 | Himmelsbach et al. |
| 2002/0173509 | A1 | 11/2002 | Himmelsbach et al. |
| 2003/0149062 | A1 | 8/2003 | Jung et al. |
| 2003/0158196 | A1 | 8/2003 | Jung et al. |
| 2003/0225079 | A1 | 12/2003 | Singer et al. |
| 2004/0158065 | A1 | 8/2004 | Barth et al. |
| 2005/0043233 | A1 | 2/2005 | Stefanic et al. |
| 2005/0085495 | A1 | 4/2005 | Soyka et al. |
| 2006/0058311 | A1 | 3/2006 | Munzert et al. |
| 2006/0100223 | A1 | 5/2006 | Himmelsbach et al. |
| 2007/0099918 | A1 | 5/2007 | Singer et al. |
| 2007/0185091 | A1 | 8/2007 | Himmelsbach et al. |
| 2008/0254040 | A1 | 10/2008 | Stefanic et al. |
| 2009/0238828 | A1 | 9/2009 | Munzert et al. |
| 2009/0306044 | A1 | 12/2009 | Solca et al. |
| 2009/0306101 | A1 | 12/2009 | Solca et al. |
| 2009/0306378 | A1 | 12/2009 | Schroeder et al. |
| 2009/0318480 | A1 | 12/2009 | Solca |
| 2010/0010023 | A1 | 1/2010 | Himmelsbach et al. |
| 2010/0069414 | A1 | 3/2010 | Himmelsbach et al. |
| 2010/0144639 | A1 | 6/2010 | Singer et al. |
| 2011/0039863 | A1 | 2/2011 | Hilberg et al. |
| 2011/0046168 | A1 | 2/2011 | Himmelsbach et al. |
| 2011/0142929 | A1 | 6/2011 | Messerschmid et al. |
| 2011/0171289 | A1 | 7/2011 | Stefanic et al. |
| 2011/0207929 | A1 | 8/2011 | Schroeder et al. |
| 2011/0207932 | A1 | 8/2011 | Schroeder et al. |
| 2012/0107399 | A1 | 5/2012 | Barta |
| 2012/0157472 | A1 | 6/2012 | Larsen et al. |

FOREIGN PATENT DOCUMENTS

| DE | 19911366 | A1 | 9/2000 |
| EP | 0302967 | A2 | 2/1989 |
| EP | 0566226 | A1 | 10/1993 |
| WO | 9520045 | A1 | 7/1995 |
| WO | 9630347 | A1 | 10/1996 |
| WO | 9633980 | A1 | 10/1996 |
| WO | 9702266 | A1 | 1/1997 |
| WO | 9738983 | A1 | 10/1997 |
| WO | 9843960 | A1 | 10/1998 |
| WO | 9906378 | A1 | 2/1999 |
| WO | 9906396 | A1 | 2/1999 |
| WO | 9909016 | A1 | 2/1999 |
| WO | 9935146 | A1 | 7/1999 |

(Continued)

OTHER PUBLICATIONS

Abstract in English (2000) for DE19911366 in German cited herein.
Fortin, S. et al., "A new Bis (2,2,2,-trifluoroethyl)phosphonate for the Synthesis of Z-Unstaurated N-Methooxy-N-methylamides". Journal Org. Chemistry, 2002, vol. 67, No. 15, p. 5437-5439.
International Search Report for PCT/EP2004/011378 mailed on May 10, 2005.
Meyer, J.K. et al., "Asymmetric Synthesis of B-Amino Acid Derivatives via Catalytic Conjugate Addition of Hydrazoic Acid to Unsaturated Imides". J. Am. Chem. Soc., 1999, 121, p. 8959-8960.
New Experimental Chemistry Course 14, Synthesis and Reaction of Organic Compounds I, Published: Nov. 20, 1977, Edited by: The Chemical Society of Japan. Issued by Shingo Iizumi, Publisher: Maruzen Company, Ltd., English Translation of section referred to by the Examiner, from the middle of p. 238 to entire p. 239.
U.S. Appl. No. 12/706,819 filed Feb. 17, 2010.
Berge, S. M. et al., "Pharmaceutical Salts", Journal of Pharmaceutical Sciences, Jan. 1977, vol. 66, No. 1, pp. 1-19.

*Primary Examiner* — Paul V. Ward
(74) *Attorney, Agent, or Firm* — Michael P. Morris; Anthony P. Bottino (57) ABSTRACT

An improved process for preparing 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline and related aminocrotonyl compounds and the preparation of a suitable salt of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline for use as a pharmaceutically active substance.

11 Claims, 2 Drawing Sheets

FOREIGN PATENT DOCUMENTS

| | | | |
|---|---|---|---|
| WO | 0031068 A1 | 6/2000 |
| WO | 0055141 A1 | 9/2000 |
| WO | WO0051991 | 9/2000 |
| WO | 0078735 A1 | 12/2000 |
| WO | WO0250043 | 6/2002 |
| WO | 03094921 A2 | 11/2003 |
| WO | 2004096224 A2 | 11/2004 |
| WO | 2005037824 A2 | 4/2005 |
| WO | 2006018182 A1 | 2/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147238 A1 | 12/2009 |
| WO | 2010081817 A1 | 7/2010 |
| WO | 2011069962 A1 | 6/2011 |

* cited by examiner

PROCESS FOR PREPARING AMINO CROTONYL COMPOUNDS

RELATED APPLICATIONS

This application is a continuation of U.S. Ser. No. 10/941,116, filed Sep. 15, 2004, which in turn claimed benefit of U.S. Ser. No. 60/517,777, filed Nov. 6, 2003, and priority from German Application No. 103 49 113.9, filed Oct. 17, 2003, each of which related applications is hereby incorporated by reference in its entirety.

FIELD OF THE INVENTION

The invention relates to an improved process for preparing aminocrotonyl compounds such as for example 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline and the physiologically acceptable salts thereof, particularly 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate, as well as 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate and the use thereof for preparing pharmaceutical compositions.

4-[(3-chloro-4-fluorophenyl)amino]-6-{[4-(N,N-dimethylamino)-1-oxo-2-buten-1-yl]-amino}-7-((S)-tetrahydrofuran-3-yloxy)-quinazoline has the following structure:

(I)

and is already known from WO 02/50043, which describes compounds with valuable pharmacological properties, including in particular an inhibiting effect on signal transduction mediated by tyrosinekinases and an inhibitory effect on signal transduction mediated by the Epidermal Growth Factor receptor (EGF-R). Therefore, compounds of this type are suitable for the treatment of diseases, particularly for the treatment of tumoral diseases, diseases of the lungs and respiratory tract and diseases of the gastrointestinal tract and bile duct and gall bladder.

WO 02/50043 discloses a method of preparation wherein aminocrotonyl compounds (IV) such as for example 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline are prepared in a one-pot reaction from the corresponding aniline component (II), bromocrotonic acid (III), oxalyl chloride and a secondary amine (see Diagram 1).

Diagram 1:

In this process the yield was at most 50%. In addition, purification was generally carried out by column chromatography. Therefore, the method of preparing 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline was not suitable on an industrial scale. Furthermore, the method had the disadvantage that bromocrotonic acid is not commercially available in large amounts and also the corresponding methyl bromocrotonate is only available in a purity of approx. 80%. These circumstances also militate against the suitability of this process for the industrial production of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline.

In the light of the above disadvantages of the known method of production, the aim of the present invention is to provide a process which allows the production of aminocrotonylarylamides, particularly 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, using highly pure starting materials which are readily available and without any great technical expenditure. This new process should therefore also be suitable for synthesis on an industrial scale and hence for commercial application.

This aim is achieved by the process according to the invention for preparing 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline and other aminocrotonyl compounds. In addition to being industrially practicable with high yields the method of synthesis according to the invention also has the advantages of very good chemical purities and a low cis content of less than 0.1%.

In the process according to the invention the corresponding aminoaryl compound (V) is reacted with a di-(C$_{1-4}$-alkyl)-phosphonoacetic acid, preferably with diethylphosphonoacetic acid, in suitable solvents, after corresponding activation, preferably with 1,1-carbonyldiimidazole, 1,1-carbonylditriazole or propanephosphonic anhydride, particularly preferably with 1,1-carbonyldiimidazole, according to Diagram 2. The solvent used may be for example tetrahydrofuran (THF), dimethylformamide (DMF) or ethyl acetate.

The activation may be carried out by any possible method of amide linking, i.e. for example with 1,1-carbonyldiimidazole, 1,1-carbonylditriazole, DCC(N,N-dicyclohexylcarbodiimide), EDC (N'-(dimethylaminopropyl)-N-ethylcarbodiimide), TBTU (O-(benzotriazol-1-yl)-N,N,N',N'-tetramethyluronium tetrafluoroborate), thiazolidine-2-thione or by conversion into the corresponding acid chloride, possibly using thionyl chloride. If desired the activation may be carried out using organic bases such as triethylamine or pyridine, while DMAP (dimethylaminopyridine) may additionally be added. Suitable solvents include DMF, THF, ethyl acetate, toluene, chlorinated hydrocarbons or mixtures thereof.

In the formulae that follow
X denotes a methyne group or a nitrogen atom,
R$_a$ denotes a benzyl, 1-phenylethyl or 3-chloro-4-fluorophenyl group and
R$^1$ denotes a straight-chain or branched C$_{1-4}$-alkyl group.

The process is preferably used for compounds wherein
X denotes a nitrogen atom,
R$_a$ denotes a 3-chloro-4-fluorophenyl group and
R$^1$ denotes an ethyl group.

Diagram 2:

a) di-(C$_{1-4}$-alkyl)-phosphonoacetic Acid, Activating Agent

The arylamide (VI) thus obtained in a high yield and high purity is reacted with the corresponding 2-aminoacetaldehyde using suitable organic or inorganic bases in the sense of a Wittig-Horner-Emmons reaction (Diagram 3). This reaction may be carried out directly or after isolation of the compound (VI), for example by precipitation by the addition of tert-butylmethyl ether, for example. Suitable bases include for example DBU (1,5-diazabicyclo[4.3.0]non-5-ene), sodium hydroxide and potassium hydroxide, of which sodium hydroxide and potassium hydroxide are preferred and potassium hydroxide is particularly preferred. Instead of the aldehyde a corresponding equivalent, e.g. a hydrate or acetal, may be used, from which the aldehyde is released (beforehand or in situ).

Diagram 3:

b) Aldehyde, Base, THF/Water

The acetals used may be for example compounds of the following general type:

wherein R$^2$ to R$^5$ in each case represent a straight-chain or branched C$_1$-C$_4$-alkyl group, while the groups may be identical or different.

Preferably
R$^3$ and R$^4$ in each case represent a methyl group and
R$^2$ and R$^5$ in each case represent an ethyl group.

The aminocrotonylarylamide of formula (VII) thus obtained, for example 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline of formula (I), may then be converted into the salts thereof, particularly the physiologically acceptable salts thereof, by methods known per se. Preferably they are converted into fumarates, tartrates or maleates. The dimaleate of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline of structural formula (Ia) and the conversion of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline into its dimaleate as shown in Diagram 4 are particularly preferred. To do this the compound (I) is dissolved in a suitable solvent, such as for example methanol, isopropanol, n-butanol or ethanol, optionally with the addition of water, preferably ethanol, and combined with crystalline maleic acid or a maleic acid solution, with heating. When ethanol is used as solvent the work is preferably done at a temperature of between 60 and 75° C. using an ethanolic maleic acid solution. The reaction conditions are preferably selected so that the desired salt crystallises out as quickly as possible. Preferably approx. 2 equivalents of maleic acid are used. After crystallisation has set in the mixture is cooled to ambient temperature, stirred and the crystals consisting of compound (Ia) are separated off.

Diagram 4:

c) Maleic Acid, Ethanol

The starting compound of formula (V) may for example be prepared as follows in accordance with methods known from the literature.

The quinoline components of formula (V), wherein X=CH, may be obtained starting from commercially obtainable 3-fluoro-6-nitrophenol (XIV) by alkylation, exchanging the fluorine atom for an amino group and reacting with ethoxyacrylic acid esters, ethoxymethylene-cyanoacetic acid esters or ethoxymethylene-malonic acid esters (Diagram 5a).

The compound thus obtained (XVII) is then converted into the compound (XVIII) as described in Diagram 6 for the quinazoline analogue Diagram 5a:

To prepare the compound (V) wherein X=N the following procedure is used:

Starting from commercially obtainable 4-chloro-anthranilic acid (VIII; X'=Cl) the quinazolinone (IX) is obtained by reaction with formamidine-acetate, and is then nitrogenated using sulphuric acid and concentrated nitric acid (Diagram 5b). Alternatively, 4-fluoro-anthranilic acid may also be used as the starting material.

Diagram 5b:

a: X' = Cl
b: X' = F
d) formamidine-acetate
e) H₂SO₄, HNO₃ conc.

The desired regioisomer (X) of the nitrogenation products thus obtained is then chlorinated, and the chlorination product (XI) is reacted in situ with the corresponding amine (Diagram 6).

Diagram 6:

f) SOCL₂, acetonitrile
g) R$_a$NH₂

The compound of formula (XII) thus obtained is reacted with (S)-(+)-3-hydroxytetrahydrofuran to form compound (XIII). Hydrogenation of compound (XIII) or compound (XVIII) from Diagram 5a then yields the starting compound (V) (diagram 7).

Diagram 7:

(XII): X = N, X' = Cl, F (XIII): X = N
(XVIII): X = CH (V)

h) (S)-(+)-3-hydroxy-tetrahydrofuran
i) H₂

The invention also relates to 4-[(3-chloro-4-fluorophenyl) amino]-6-{[4-(N,N-dimethylamino)-1-oxo-2-buten-1-yl] amino}-7-((S)-tetrahydrofuran-3-yloxy)-quinazoline dimaleate. This salt is particularly suitable for pharmaceutical use as it exists in only one crystalline modification, which is moreover anhydrous and very stable.

For pharmaceutical use an active substance not only has to exhibit the desired activity, but must also conform to additional requirements in order to be allowed to be used as a pharmaceutical composition. These parameters are to a large extent connected with the physicochemical nature of the active substance.

Without being restrictive, examples of these parameters are the stability of effect of the starting material under various environmental conditions, stability during production of the pharmaceutical formulation and stability in the final medicament compositions. The pharmaceutically active substance used for preparing the pharmaceutical compositions should therefore have a high stability which must be guaranteed even under various environmental conditions. This is absolutely essential to prevent the use of pharmaceutical compositions which contain, in addition to the actual active substance, breakdown products thereof, for example. In such cases the content of active substance in pharmaceutical formulations might be less than that specified.

The absorption of moisture reduces the content of pharmaceutically active substance on account of the weight gain caused by the uptake of water. Pharmaceutical compositions with a tendency to absorb moisture have to be protected from damp during storage, e.g. by the addition of suitable drying agents or by storing the medicament in a damp-proof environment. In addition, the uptake of moisture can reduce the content of pharmaceutically active substance during manufacture if the medicament is exposed to the environment without being protected from damp in any way. Preferably a pharmaceutically active substance should therefore have only limited hygroscopicity.

As the crystal modification of an active substance is important to the reproducible active substance content of a preparation, there is a need to clarify as far as possible any existing polymorphism of an active substance present in crystalline form. If there are different polymorphic modifications of an active substance care must be taken to ensure that the crystalline modification of the substance does not change in the pharmaceutical preparation later produced from it. Otherwise, this could have a harmful effect on the reproducible potency of the drug. Against this background, active substances characterised by only slight polymorphism are preferred.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible. This problem is solved by 4-[(3-chloro-4-fluorophenyl)amino]-6-{[4-(N,N-dimethyl-amino)-1-oxo-2-buten-1-yl]amino}-7-((S)-tetrahydrofuran-3-yloxy)-quinazoline dimaleate.

Figure 1:
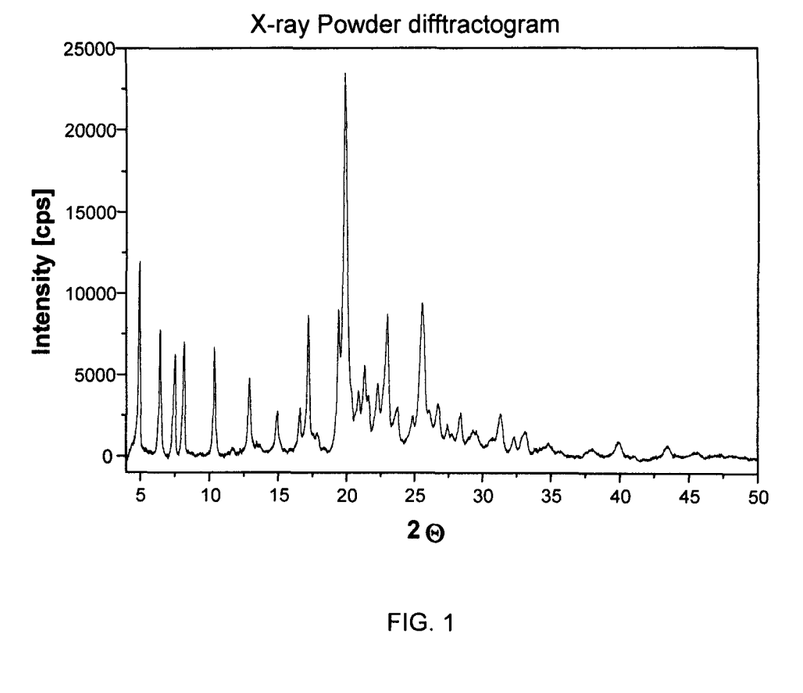
FIG. 1 is an X-ray powder diffractogram of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate.
Figure 2:
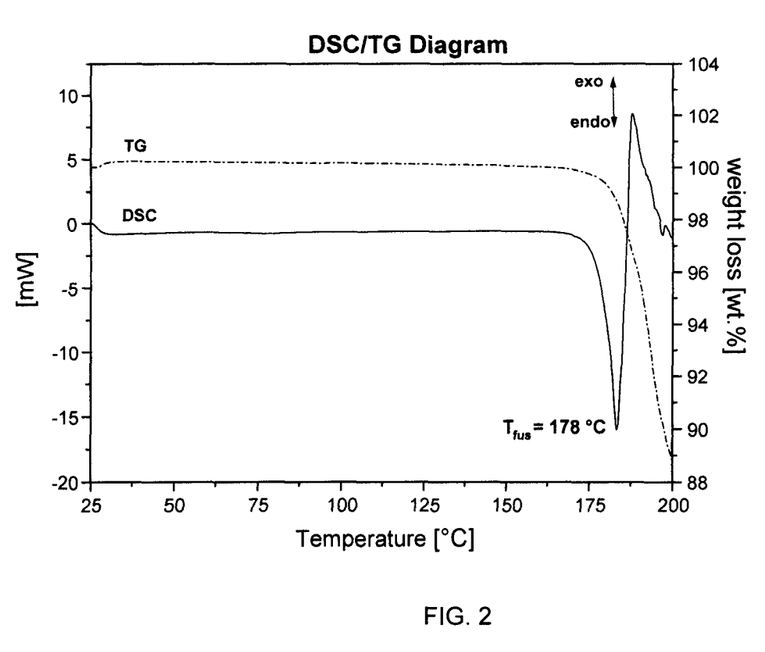
FIG. 2 is a diagram depicting Thermoanalysis of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate.

4-[(3-chloro-4-fluorophenyl)amino]-6-{[4-(N,N-dimethylamino)-1-oxo-2-buten-1-yl]-amino}-7-((S)-tetrahydrofuran-3-yloxy)-quinazoline dimaleate has a melting point of 178° C. (cf. the thermoanalysis shown in FIG. 2). The crystalline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate was investigated further by X-ray powder diffraction. The diagram obtained is shown in FIG. 1.

The following Table lists the data obtained in this analysis:

TABLE

X-ray powder reflections and intensities (standardised) of the 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate

| 2-Θ [°] | d-value [Å] | intensity $I/I_o$ [%] |
|---|---|---|
| 4.91 | 18.0 | 47 |
| 6.42 | 13.8 | 33 |
| 7.47 | 11.8 | 27 |
| 8.13 | 10.9 | 30 |
| 10.37 | 8.53 | 30 |
| 11.69 | 7.56 | 2 |
| 12.91 | 6.85 | 20 |
| 13.46 | 6.58 | 3 |
| 13.66 | 6.48 | 2 |
| 14.94 | 5.93 | 11 |
| 16.58 | 5.34 | 12 |
| 17.19 | 5.15 | 36 |
| 17.87 | 4.96 | 5 |
| 19.43 | 4.57 | 38 |
| 19.91 | 4.46 | 100 |
| 20.84 | 4.26 | 13 |
| 21.33 | 4.16 | 21 |
| 21.58 | 4.12 | 12 |
| 22.25 | 3.992 | 15 |
| 22.94 | 3.873 | 32 |
| 23.67 | 3.756 | 9 |
| 24.82 | 3.584 | 7 |

TABLE-continued

X-ray powder reflections and intensities (standardised) of the 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate

| 2-Θ [°] | d-value [Å] | intensity $I/I_o$ [%] |
|---|---|---|
| 25.56 | 3.482 | 37 |
| 26.71 | 3.335 | 9 |
| 27.46 | 3.245 | 4 |
| 28.37 | 3.143 | 8 |
| 30.71 | 2.909 | 3 |
| 29.31 | 3.045 | 4 |
| 29.57 | 3.019 | 4 |
| 31.32 | 2.854 | 10 |
| 32.31 | 2.769 | 4 |
| 33.10 | 2.705 | 5 |
| 33.90 | 2.643 | 1 |
| 34.84 | 2.573 | 2 |
| 35.71 | 2.512 | 1 |
| 36.38 | 2.467 | 1 |
| 36.96 | 2.430 | 1 |
| 37.99 | 2.367 | 2 |
| 39.94 | 2.255 | 5 |

In the preceding Table the value "2Θ[°]" denotes the angle of diffraction in degrees and the value "$d_{hkl}$ [Å]" denotes the specified distances in Å between the lattice planes.

The x-ray powder diagrams were recorded, within the scope of the present invention, using a Bruker D8 Advanced diffractometer fitted with a PSD detector and a Cu anode as the x-ray source (CuK$_{\alpha_1}$ radiation, λ=1.5418 Å, 40 kV, 40 mA).

The following Examples are intended to illustrate the invention:

EXAMPLES

Example 1

Diethyl {[4-(3-chloro-4-fluoro-phenylamino)-7-((S)-tetrahydrofuran-3-yloxy)-quinazolin-6-ylcarbamoyl]-methyl}-phosphonate -continued

3.58 kg of 1,1-carbonyldiimidazole (22.16 mol) are placed in 12.8 liters of tetrahydrofuran and at 40° C. combined with 4.52 kg (22.16 mol) of diethylphosphonoacetic acid dissolved in 6.5 liters of tetrahydrofuran. The mixture is stirred for 30 minutes at 40° C. The resulting solution is referred to as solution A.

6.39 kg (17.05 mol) of $N^4$-(3-chloro-4-fluoro-phenyl)-7-(tetrahydrofuran-3-yloxy)quinazoline-4,6-diamine are placed in 26.5 liters of tetrahydrofuran and at 40° C. combined with solution A and stirred for 2 hours at 30° C. 64 liters of tert.-butylmethylether are added to the suspension and after cooling to 20° C. the precipitate is removed by centrifuging. It is washed with a mixture of 16 liters of tetrahydrofuran and 16 liters of tert.-butylmethylether and then with 32 liters of water and dried at 50° C.

Yield: 6.58 kg (69.8%) of white crystals, content: HPLC 99.1 Fl %

Example 2

(E)-4-dimethylamino-but-2-enoic acid-[4-(3-chloro-4-fluoro-phenylamino)-7-((S)-tetrahydrofuran-3-yloxy)-quinazolin-6yl]-amide 5.6 liters of 30% hydrochloric acid (53.17 mol) are added to 4.4 liters of water. Then 4.28 kg of 95% (dimethylamino)-acetaldehyde-diethylacetal (26.59 mol) are added dropwise within 20 minutes at 30° C. The reaction solution is stirred for 8 hours at 35° C. stirred, cooled to 5° C. and stored under argon. This solution is referred to as solution B.

4.55 kg (68.06 mol) of potassium hydroxide are dissolved in 23.5 liters of water and cooled to −5° C. This solution is referred to as solution C.

5.88 kg (10.63 mol) of diethyl ((4-(3-chloro-4-fluoro-phenylamino)-7-(tetrahydrofuran-3-yloxy)-quinazoline-6-yl-carbamoyl)-methyl)-phosphonate and 0.45 kg of lithium chloride (10.63 mol) are placed in 23.5 liters of tetrahydrofuran and cooled to −7° C. The cold solution C is added within 10 minutes. Then solution B is added at −7° C. within 1 hour. After stirring for a further hour at −5° C. the reaction mixture is heated to 20° C. and combined with 15 liters of water. After cooling to 3° C. the suspension is suction filtered, the precipitate is washed with water and dried. Yield: 5.21 kg of crude product, 100%, water content: 6.7%

The crystallisation of the crude product is carried out with butyl acetate/methylcyclohexane Yield: 78% purity HPLC 99.4 Fl %, water content 5.4%

Example 3

(E)-4-dimethylamino-but-2-enoic acid-(4-(3-chloro-4-fluoro-phenylamino)-7-((S)-tetra-hydrofuran-3-yloxy)-quinazolin-6yl)-amide dimaleate 6.0 kg (12.35 mol) of (E)-4-dimethylamino-but-2-enoic acid-(4-(3-chloro-4-fluoro-phenylamino)-7-((S)-tetrahydro-furan-3-yloxy)-quinazolin-6-yl)-amide are placed in 84 litres of ethanol and heated to 70° C. and combined with a solution of 2.94 kg (25.31 mol) of maleic acid in 36 liters of ethanol. After crystallisation has set in, first the mixture is cooled to 20° C. and stirred for 2 hours, then for 3 hours at 0° C. The precipitate is suction filtered, washed with 19 liters of ethanol and dried in vacuo at 40° C.

Yield: 8.11 kg (91.5%)
Melting point: 178° C.
$^1$H-NMR (CD$_3$OD): δ=2.47+2.27 (m+m, 2H), 2.96 (s, 6H), 4.03 (m, 2H), 4.07+3.92 (m+m, 2H), 4.18+4.03 (m+m, 2H), 5.32 (m, 1H), 6.26 (s, 4H), 6.80 (m, 1H), 6.99 (m, 1H), 7.27(s, 1H), 7.30 (t, 1H), 7.66 (m, 1H), 7.96 (dd, 1H), 8.62 (s, 1H), 9.07 (s, 1H) ppm

What is claimed is:

1. A process for preparing a compound of the formula (VII)

wherein X denotes a methyne group or a nitrogen atom,
$R_a$ denotes a benzyl, 1-phenylethyl or 3-chloro-4-fluorophenyl group and
$R^3$ and $R^4$ denote a straight-chain or branched $C_{1-4}$-alkyl group, comprising the following synthesis steps:
a) reacting a compound of the formula (V)

(V)

wherein X denotes a methyne group or a nitrogen atom and
$R_a$ denotes a benzyl, 1-phenylethyl or 3-chloro-4-fluorophenyl group, in suitable solvents after corresponding activation with di-($C_{1-4}$-alkyl)-phosphonoacetic acid and b) reacting the resulting compound of the formula (VI)

(VI)

wherein X denotes a methyne group or a nitrogen atom,
$R_a$ denotes a benzyl, 1-phenylethyl or 3-chloro-4-fluorophenyl group and
$R^1$ denotes a straight-chain or branched $C_{1-4}$-alkyl group, with the aldehyde of formula wherein $R^3$ and $R^4$ in each case represent a straight-chain or branched $C_1$-$C_4$-alkyl group, while the groups may be identical or different,
or a corresponding aldehyde equivalent, using suitable organic or inorganic bases.

2. A process for preparing 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, comprising the following synthesis steps:
a) reacting $N^4$-(3-chloro-4-fluoro-phenyl)-7-(tetrahydrofuran-3-yloxy)quinazoline-4,6-diamine in suitable solvents after corresponding activation with di-($C_{1-4}$-alkyl)-phos-phonoacetic acid and
b) reacting the resulting dialkylester {[4-(3-chloro-4-fluoro-phenylamino)-7-((S)-tetrahydrofuran-3-yloxy)-quinazolin-6-ylcarbamoyl]-methyl}-phosphonate with the aldehyde prepared in situ from the corresponding (dimethylamino)-acetaldehyde-dialkylacetal using suitable organic or inorganic bases.

3. The process according to claim 2, wherein in step a) diethylphosphonoacetic acid is used as reagent.

4. The process according to claim 1, wherein in step b) DBU (1,5-diaza-bicyclo[4.3.0]non-5-ene), sodium hydroxide or potassium hydroxide is used as base.

5. The process according to claim 4, wherein in step b) potassium hydroxide is used as base.

6. A process for preparing the dimaleates of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, comprising steps a and b according to claim 1 as well as the following step c):
c) converting the resulting 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline into the dimaleate by reacting with maleic acid in a suitable solvent, with heating.

7. The process according to claim 6, wherein ethanol or isopropanol is used as solvent, optionally with the addition of water.

8. The process according to claim 6, wherein at least 2equivalents of maleic acid are used.

9. Crystalline 4-[(3-chloro-4-fluorophenyl)amino]-6-{[4-(N,N-dimethylamino)-1-oxo-2-buten-1-yl]amino}-7-((S))-tetrahydofuran-3-yloxy)-quinazoline dimaleate, characterized by 2 Θ [°] values obtained by X-ray powder diffraction using $CuK_{\alpha 1}$ radiation, $\lambda$=1.5418Å in the following table:

| 2-Θ [°] | intensity $I/I_o$ [%] |
| --- | --- |
| 4.91 | 47 |
| 6.42 | 33 |
| 7.47 | 27 |
| 8.13 | 30 |
| 10.37 | 30 |
| 17.19 | 36 |
| 19.43 | 38 |
| 19.91 | 100 |
| 21.33 | 21 |
| 22.94 | 32 |
| 25.56 | 37. |

10. Crystalline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate, characterized by 2 Θ [°] values obtained by X-ray powder diffraction using $CuK_{\alpha 1}$ radiation, $\lambda$=1.5418 Å in the following table:

| 2-Θ [°] | intensity $I/I_o$ [%] |
| --- | --- |
| 4.91 | 47 |
| 6.42 | 33 |
| 7.47 | 27 |
| 8.13 | 30 |
| 10.37 | 30 |
| 12.91 | 20 |
| 14.94 | 11 |
| 16.58 | 12 |
| 17.19 | 36 |
| 19.43 | 38 |
| 19.91 | 100 |
| 20.84 | 13 |
| 21.33 | 21 |

-continued

| 2-Θ [°] | intensity I/I₀ [%] |
|---|---|
| 21.58 | 12 |
| 22.25 | 15 |
| 22.94 | 32 |
| 25.56 | 37. |

11. Crystalline 4-[(3-chloro-4-fluorophenyl)amino]-6-{[4-(N,N-dimethylamino)-1-oxo-2-buten-1-yl]amino}-7-((S))-tetrahydofuran-3-yloxy)-quinazoline dimaleate, characterized by 2 Θ [°] values obtained by X-ray powder diffraction using CuK$_{α1}$ radiation, λ=1.5418 Å in the following table:

| 2-Θ [°] | d-value [Å] | intensity I/I₀ [%] |
|---|---|---|
| 4.91 | 18.0 | 47 |
| 6.42 | 13.8 | 33 |
| 7.47 | 11.8 | 27 |
| 8.13 | 10.9 | 30 |
| 10.37 | 8.53 | 30 |
| 11.69 | 7.56 | 2 |
| 12.91 | 6.85 | 20 |
| 13.46 | 6.58 | 3 |
| 13.66 | 6.48 | 2 |
| 14.94 | 5.93 | 11 |
| 16.58 | 5.34 | 12 |

-continued

| 2-Θ [°] | d-value [Å] | intensity I/I₀ [%] |
|---|---|---|
| 17.19 | 5.15 | 36 |
| 17.87 | 4.96 | 5 |
| 19.43 | 4.57 | 38 |
| 19.91 | 4.46 | 100 |
| 20.84 | 4.26 | 13 |
| 21.33 | 4.16 | 21 |
| 21.58 | 4.12 | 12 |
| 22.25 | 3.992 | 15 |
| 22.94 | 3.873 | 32 |
| 23.67 | 3.756 | 9 |
| 24.82 | 3.584 | 7 |
| 25.56 | 3.482 | 37 |
| 26.71 | 3.335 | 9 |
| 27.46 | 3.245 | 4 |
| 28.37 | 3.143 | 8 |
| 30.71 | 2.909 | 3 |
| 29.31 | 3.045 | 4 |
| 29.57 | 3.019 | 4 |
| 31.32 | 2.854 | 10 |
| 32.31 | 2.769 | 4 |
| 33.10 | 2.705 | 5 |
| 33.90 | 2.643 | 1 |
| 34.84 | 2.573 | 2 |
| 35.71 | 2.512 | 1 |
| 36.38 | 2.46 | 71 |
| 36.96 | 2.430 | 1 |
| 37.99 | 2.367 | 2 |
| 39.94 | 2.255 | 5. |

* * * * *

UNITED STATES PATENT AND TRADEMARK OFFICE
CERTIFICATE OF CORRECTION

| | |
|---|---|
| PATENT NO. | : 8,426,586 B2 |
| APPLICATION NO. | : 11/457622 |
| DATED | : April 23, 2013 |
| INVENTOR(S) | : Rainer Soyka et al. |

It is certified that error appears in the above-identified patent and that said Letters Patent is hereby corrected as shown below:

In the Specification

In column 16, line 25, change "36.38  2.46  71" to

-- 36.38  2.467  1 --.

Signed and Sealed this
Twenty-first Day of July, 2015

Michelle K. Lee
*Director of the United States Patent and Trademark Office*